United States Patent [19]

Curnutt

[11] Patent Number: 4,625,044

[45] Date of Patent: Nov. 25, 1986

[54] PROCESS OF PREPARING DIHYDROCARBYL CARBONATES USING A NITROGEN-CONTAINING COORDINATION COMPOUND SUPPORTED ON ACTIVATED CARBON

[75] Inventor: Gerald L. Curnutt, Midland, Mich.

[73] Assignee: The Dow Chemical Company, Midland, Mich.

[21] Appl. No.: 612,163

[22] Filed: May 21, 1984

[51] Int. Cl.$^4$ .............................................. C07C 68/04
[52] U.S. Cl. ................................. 558/277; 558/260; 558/270; 558/274
[58] Field of Search ........................................ 260/463

[56] References Cited

U.S. PATENT DOCUMENTS

| | | | |
|---|---|---|---|
| 3,846,468 | 11/1974 | Perrotti et al. | 260/463 |
| 3,980,690 | 9/1976 | Cipriani et al. | 260/463 |
| 4,370,275 | 1/1983 | Stammann et al. | 260/463 |
| 4,426,331 | 1/1984 | Drent | 260/463 |

*Primary Examiner*—Donald G. Daus
*Assistant Examiner*—Stephen M. Kapner

[57] ABSTRACT

The invention is a composition which comprises a nitrogen-containing coordination compound copper hydrocarbyloxy halide complex supported on activated carbon. This composition is useful as a catalyst for the preparation of dihydrocarbyl carbonates from alcohols, carbon monoxide and oxygen.

13 Claims, No Drawings

PROCESS OF PREPARING DIHYDROCARBYL CARBONATES USING A NITROGEN-CONTAINING COORDINATION COMPOUND SUPPORTED ON ACTIVATED CARBON

BACKGROUND OF THE INVENTION

This invention relates to novel nitrogen-containing coordination compound copper hydrocarbyloxy halide complexes supported on activated carbon. These novel compositions are useful in the preparation of dihydrocarbyl carbonates.

The carbonates produced by this invention are well-known and are useful as synthetic lubricants, solvents, and chemical intermediates in the preparation of pharmaceutically active compounds and in the preparation of polymeric derivatives, for example, clear plastics.

Carbonates are typically produced by contacting phosgene with the appropriate alcohol. See Drake et al., J. Am. Chem. Soc., 52, 3720 (1960) and U.S. Pat. No. 2,379,250. The hydrogen chloride that is produced by this process is not easily eliminated and leads to the production of chlorine-containing products. Attempts to neutralize the hydrogen chloride, e.g., with an acid acceptor, have led to processing difficulties. Moreover, when secondary alcohols are employed, the competing reaction involving alkyl chloride formation is serious and necessitates the use of an acid acceptor.

Frevel et al., U.S. Pat. No. 3,642,858, disclose that carbonates can be prepared by reacting a cyclic alkylene carbonate with a nontertiary hydroxy-containing compound in the presence of a catalytic amount of an alkali metal.

Gaenzler et al., U.S. Pat. No. 3,952,045, disclose a method for preparing carbonates which comprises reacting an alcohol, with carbon monoxide and oxygen, in the presence of a catalyst comprising a copper salt, chloride or bromide, and an organic phosphorus compound.

Romano et al., U.S. Pat. No. 4,218,391, disclose the preparation of carbonates by reacting an alcohol with oxygen and carbon monoxide in the presence of a catalyst which is a salt of a metal belonging to Groups IB, IIB, and VIII of the Periodic Table; the least possible number of inorganic anions is desirable in order to reduce the acidity of the environment as far as possible. The salts of monovalent copper are preferred.

Stammann et al., U.S. Pat. No. 4,370,275, disclose a process for the preparation of carbonates wherein an alcohol is reacted with a mixture of molecular oxygen and carbon monoxide in the liquid phase in the presence of a catalyst containing copper, chemically bonded oxygen, chemically bonded halogen and at least one nitrogen base.

Cipriani et al., U.S. Pat. No. 3,980,690, disclose the preparation of a carbonate which comprises reacting an alcohol with oxygen and carbon monoxide in the presence of a catalyst in the heterogeneous phase by introducing the reactants into a reactor charged with a catalyst such as the complex of a system formed by copper chloride and 4-vinylpyridine, causing the reactants to flow over the catalyst, and then withdrawing the products of the reaction and unconsumed reactants from the reactor. It is taught that in order to obtain the catalyst described in the invention, use may be made of salts of metals belonging to the IB, II and VIII Groups of the Periodic system. For instance, salts of metals selected from among copper, silver, gold, zinc, cadmium, mercury, iron and nickel. The most suitable anions, to which the metal ion is bound, are selected from halides, $CN-$, $ClO_4-$ or complex ions of the $BF_4-$ type and the like.

Perrotti et al., U.S. Pat. No. 3,846,468, describe a process for the preparation of carbonates which comprises reacting an alcohol with oxygen and carbon monoxide in the presence of a catalyst which is copper complexed with an inorganic molecule. The catalyst disclosed generally corresponds to the formula $MX_nL_m$ wherein M is a metal of IB, IIB or Group VIII of the Periodic system, preferably copper, silver, gold, zinc, cadmium, mercury, iron, cobalt, nickel, that is, metals able to exist in two different valence states by means of redox reactions; X is an anion; and L is a neutral ligand. More suitable anions are halide ions, cyanate ions, hypochlorate ions, and complex anions of $BF_4-$ and the like. The ligands are selected from the group consisting of organic bases such as pyridine, dipyridyl, imidazole, phenanthroline, alkyl or aryl phosphines, dimethyl sulfoxide, dimethylformamide, quinuclidine, carbon monoxide, suitable ligands are also the nitriles such as acetonitrile, cyanobenzene, and the bidentate ligands such as malonitrile, succinodinitrile, adiponitrile and the like.

Hallgren et al., U.S. Pat. No. 4,361,519, disclose a process for the preparation of carbonates which comprises contacting an alcohol, carbon monoxide, a Bronsted base, a Group VIIIB element, oxygen and a redox cocatalyst.

Hallgren et al., U.S. Pat. No. 4,360,477, disclose the preparation of alkyl carbonates by carbonylation of alkanols with carbon monoxide and oxygen at elevated temperatures in the presence of certain copper salts.

The processes described hereinbefore generally demonstrate slow kinetics and have poor selectivity towards the desired carbonates under conditions which are suitable for commercial processes. Furthermore, many of the processes result in the presence of metal salts, such as copper halide salts, being present during the process. Such metal salts are generally corrosive and create significant problems in processing.

The methods described hereinbefore utilizing a homogeneous or slurry process require the use of elaborate separation techniques to separate the organic base promoter and the azeotropic mixtures of dimethyl carbonate formed with the by-product water and methanol which is generally used as the solvent. Additionally, the water accumulates in the solvent and rapidly deactivates the copper halide catalyst.

What is needed is a process for the preparation of carbonates wherein the rate of reaction is reasonable, the selectivity towards carbonates is high and there are no corrosive elements present so as to create significant problems in processing. What is further needed is a heterogeneous catalyst which meets these criteria.

SUMMARY OF THE INVENTION

The invention is a composition which comprises a nitrogen-containing coordination compound copper hydrocarbyloxy halide complex supported on activated carbon.

Another aspect of this invention is a process for the preparation of a dihydrocarbyl carbonate which comprises contacting oxygen, carbon monoxide, and an alcohol, wherein the alcohol can be vaporized under the reaction conditions, in the vapor phase in the presence of a catalyst which comprises the complex described hereinbefore, under conditions such that a dihydrocarbyl carbonate is prepared.

The complex of this invention serves as heterogeneous catalyst for the preparation of dihydrocarbyl carbonate and the use of such complex as a catalyst results in good reaction kinetics and rates. Furthermore, there are no corrosive elements and the products can be recovered relatively easily.

DETAILED DESCRIPTION OF THE INVENTION

The novel composition of this invention is a basic nitrogen-containing coordination compound copper hydrocarbyloxy halide complex, on an activated carbon support. As described hereinafter, the complex is prepared from its various components and then thereafter placed on an activated carbon support.

The basic nitrogen-containing coordination compound can be any nitrogen-containing compound which will complex with copper halides and hydrocarbyloxy moieties. Desirable nitrogen-containing coordination compounds include ammonia, primary amines, secondary amines, heterocyclic amines, aromatic amines, organic nitriles, ethylenediamine and alkyl-substituted ethylenediamines, and the oligomers of ethylenimine.

Primary amines useful in this invention include aminomethane, aminoethane, 1-aminopropane, 1-amino-1-methylethane, 1-aminobutane, 1-amino-2-methylpropane, 1-amino-1,1-dimethylethane, aminopentanes, aminohexanes, aminocyclohexane, aminoheptanes, aminooctanes, aminododecanes, aminooctadecanes, aminoeicosane, aminotriacontanes, benzylamine, chlorobenzylamine, nitrobenzylamine, 2-ethoxyethylamine, 4-carbomethoxyhexylamine, aniline, toluidine, anisidine, nitroaniline, bromoaniline, xylidines, 4-ethylaniline, and naphthylamine.

Secondary amines include dimethylamine, diethylamine, di-n-propylamine, diisopropylamine, di-n-butylamine, di-sec-butylamine, diisobutylamine, di-t-butylamine, dipentylamines, dihexylamines, dioctylamines, ditriacontanylamines, n-methylethylamine, n-methylpropylamine, n-methyloctadecylamine, n-ethylhexylamine, n-ethyldodecylamine, n-propyldodecylamine, diphenylamine, n-phenylnaphthylamine, n-ethylaniline, n-methyl-o-toluidine, n-methyl-p-toluidine, p-chloro-n-methylaniline, N,N'-dimethylphenylenediamine, 4-ethylaniline, 4-propylaniline, 4-butylaniline, 4-decylaniline.

Heterocyclic secondary amines include piperazine, pyrrole, imidazoline, pyrazole, 2-methylpiperadine, pyrrolidine, oxazolidine, morpholine and ethylenimine.

Aromatic nitrogen compounds include imidazole, triazole, tetrazole, pyridine, 2,4,6-trimethylpyridine, dimethylaminopyridine, benzimidazole, benzotriazole, 2-(5-aminopentyl)benzimidazole, 1,2-pentamethylenebenzimidazole and quinoline. Nitriles include acetonitrile, benzonitrile, malonitrile, succinodinitrile, and adiponitrile. Preferred basic nitrogen compounds include trialkylamines, triethylenediamine, pyridine, a substituted pyridine, imidazole, piperidine, ammonia or acetonitrile.

More preferred basic nitrogen compounds are pyridine, substituted derivatives of pyridine, ammonia and acetonitrile, with pyridine being the most preferred.

The halide can be bromide, chloride or iodide, with chloride and bromide being preferred. Chloride is the most preferred halide.

The hydrocarbyloxy moiety corresponds to the alcohol to be used to form the dihydrocarbyl carbonate. The hydrocarbyloxy moiety corresponds to the residue of any alcohol which can be vaporized under the reaction conditions of the formation of the dihydrocarbyl carbonate. Preferred hydrocarbyloxy moieties include $C_{1-6}$ alkoxy, $C_{3-6}$ cycloalkoxy, and benzoxy. More preferred hydrocarbyloxy moieties are the $C_{1-6}$ alkoxy moieties, with even more preferred hydrocarbyloxy moieties being methoxy, ethoxy, or propoxy. The most preferred hydrocarbyloxy moiety is methoxy.

Examples of the complexes used in this invention include, pyridine copper methoxychloride, pyridine copper ethoxychloride, pyridine copper propoxychloride, pyridine copper butoxychloride, pyridine copper methoxybromide, pyridine copper ethoxybromide, pyridine copper propoxybromide, pyridine copper butoxybromide, 2,4,6-trimethylpyridine copper methoxychloride, 2,4,6-trimethylpyridine copper ethoxychloride, 2,4,6-trimethylpyridine copper propoxychloride, 2,4,6-trimethylpyridine copper butoxychloride, 2,4,6-trimethylpyridine copper methoxybromide, 2,4,6-trimethylpyridine copper ethoxybromide, 2,4,6-trimethylpyridine copper propoxybromide, 2,4,6-trimethylpyridine copper butoxybromide, 4-dimethylaminopyridine copper methoxychloride, 4-dimethylaminopyridine copper ethoxychloride, 4-dimethylaminopyridine copper propoxychloride, 4-dimethylaminopyridine copper butoxychloride, 4-dimethylaminopyridine copper methoxybromide, 4-dimethylaminopyridine copper ethoxybromide, 4-dimethylaminopyridine copper propoxybromide, and 4-dimethylaminopyridine copper butoxybromide. Preferred complexes are pyridine copper methoxychloride, pyridine copper ethoxychloride, pyridine copper propoxychloride, pyridine copper butoxychloride, pyridine copper methoxybromide, pyridine copper ethoxybromide, pyridine copper propoxybromide, and pyridine copper butoxybromide. More preferred complexes are pyridine copper methoxychloride, pyridine copper ethoxychloride, and pyridine copper propoxychloride, with pyridine copper methoxychloride being most preferred.

The activated carbon can be any activated carbon which is presently known in the art. Preferred activated carbons are those derived from lignite, with more preferred activated carbons being those derived from lignite which have been acid washed. A particularly preferred activated carbon is a Darco ® activated carbon (available by ICI Americas, Inc.).

In one preferred embodiment, a sufficient amount of complex is placed on the activated carbon so that there is between about 0.01 and 50 percent by weight of copper on the carbon. In a more preferred embodiment, a sufficient amount of complex is placed on the activated carbon support to provide between about 1 and 10 percent by weight of copper.

The complex described hereinbefore can be prepared by dissolving the nitrogen-containing complexing compound in an alcohol, wherein the hydrocarbon portion of the alcohol corresponds to the hydrocarbon portion of the hydrocarbyloxy group on the complex to be prepared. Thereafter, a cuprous halide is added to the solution to prepare a slurry while anhydrous oxygen is bubbled into the solution. The oxygen is bubbled through the mixture for between about 10 and 20 hours at a temperature of between 20° C. and 30° C. The complex precipitates out of the solution. The complex can be separated by filtration methods. The complex can thereafter be dried to remove any of the alcohol present. It may be desirable to prepare the complex in the presence of a drying agent, as water may be formed in the preparation of the complex which may deactivate the catalyst.

The complex can be placed on the support by incipient wetness techniques, which are well-known in the art. In practice, the complex is dissolved in pyridine and the solution of complex and pyridine is contacted with the activated carbon to impregnate the activated carbon with the complex. After the contacting, the impregnated carbon is dried to remove any excess pyridine.

The novel compositions prepared in such a manner can then be used for the preparation of dihydrocarbyl carbonates. In general, the process involves contacting carbon monoxide, oxygen, and an alcohol which is vaporizable under the reaction conditions, in the presence of the catalyst composition described hereinbefore.

Alcohols useful in this invention include any alcohol which is vaporizable under the reaction conditions. Preferred alcohols correspond to the formula $R^1OH$ wherein $R^1$ is $C_{1-6}$ alkyl, $C_{3-6}$ cycloalkyl, or benzyl. $R^1$ is preferably $C_{1-6}$ alkyl, more preferably methyl, ethyl or propyl, and most preferably methyl.

Preferred alcohols include methanol, ethanol, propanol, butanol, pentanol, hexanol, cyclopropanol, cyclobutanol, cyclopentanol, cyclohexanol, and benzyl alcohol. More preferred alcohols are methanol, ethanol, propanol, butanol, pentanol, and hexanol. Even more preferred alcohols are methanol, ethanol, or propanol, with methanol being most preferred.

This process prepares dihydrocarbyl carbonates, wherein the hydrocarbyl moiety corresponds to the hydrocarbon portion of the alcohol used in the preparation. Preferred carbonates correspond to the formula $$R^1O-\overset{O}{\underset{\|}{C}}-OR^1$$

wherein $R^1$ is $C_{1-6}$ alkyl, $C_{3-6}$ cycloalkyl, or benzyl. $R^1$ is preferably $C_{1-6}$ alkyl, more preferably methyl, ethyl or propyl, and most preferably methyl.

Examples of carbonates prepared by this invention include dimethyl carbonate, diethyl carbonate, dipropyl carbonate, dibutyl carbonate, dipentyl carbonate, dihexyl carbonate, dicyclopropyl carbonate, dicyclobutyl carbonate, dicyclopentyl carbonate, dicyclohexyl carbonate, dibenzyl carbonate, and the like. Preferred carbonates prepared by this process include dimethyl carbonate, diethyl carbonate, dipropyl carbonate, dibutyl carbonate, dipentyl carbonate and dihexyl carbonate. Even more preferred carbonates are dimethyl carbonate, diethyl carbonate, and dipropyl carbonate. The most preferred carbonate prepared by this invention is dimethyl carbonate.

In general, the alcohol or mixture of alcohols is contacted with oxygen and carbon monoxide under carbonylation conditions so as to prepare a carbonate. In the embodiment wherein a mixture of alcohols is used, the carbonates prepared are a mixture of symmetrical and unsymmetrical carbonates. When a single alcohol is used, the product is symmetrical carbonate. The symmetrical dihydrocarbyl carbonates are the preferred carbonates.

The process of this invention involves contacting carbon monoxide, oxygen and an alcohol in the vapor phase and passing them over the novel catalyst composition described hereinbefore. The process of this invention can be illustrated by the equation $$2R^1OH + \tfrac{1}{2}O_2 + CO \longrightarrow R^1-O\overset{O}{\underset{\|}{C}}O-R^1 + H_2O$$

wherein $R^1$ is as defined hereinbefore. The ratio of carbon monoxide to the alcohol can be any mole ratio which results in the preparation of the dihydrocarbyl carbonates. Preferably, the ratio of carbon monoxide the alcohol is between about 1:1 and 1000:1 moles. More preferably, the ratio of carbon monoxide to alcohol is between 1:1 and 100:1 moles, and most preferably the ratio of carbon monoxide to alcohol is between about 1:1 and 10:1 moles. The ratio of oxygen to alcohol is any ratio which results in the preparation of the dihydrocarbyl carbonates. Preferably, the ratio of oxygen to alcohol is between about 1:1 and 1:1000 moles. More preferably the ratio of oxygen to alcohol is between 1:1 and 1:100 moles. Most preferably the ratio of oxygen to alcohol is between 1:1 and 1:10 moles. The ratio of oxygen to carbon monoxide is any ratio which results in the preparation of the dihydrocarbyl carbonates. Preferably, the ratio of oxygen to carbon monoxide is between 1:1 and 1:1000 moles. More preferably the ratio of oxygen to carbon monoxide is between 1:1 and 1:100 moles, and most preferably the ratio of oxygen to carbon monoxide is between 1:1 and 1:10 moles.

The oxygen can be added to the reaction mixture as pure molecular oxygen or diluted with an inert gas such as nitrogen or argon. It is preferred to keep the oxygen concentration at no more than 10 mole percent of the entire reaction feed so as to avoid the formation of explosive mixtures.

This process can be performed at any temperature at which the reaction proceeds. Preferred temperatures are between about 20° C. and 150° C., with between about 90° C. and 125° C. being more preferred. The most preferred temperatures are between about 115° C. and 125° C. The pressure can be atmospheric or superatmospheric pressure. Preferred pressures are between 1 and 100 atmospheres, with between 15 and 25 atmospheres being most preferred.

The reaction mixture feed gas flow rate expressed as gas hourly space velocity can be between about 100 and 50,000 (Hr.$^{-1}$), and most preferably between about 1,000 and 2,000 (Hr.$^{-1}$). The dihydrocarbyl carbonate can be recovered from the reaction mixture by methods well-known in the art, one particularly desirable method is the use of extractive distillation of the condensed reaction product.

The process of this invention can be performed in either a fixed or fluid bed reactor using either continuous or batch processing methods. It is preferred to use a fixed bed reactor and a continuous mode of operation.

In one most preferred embodiment, the dihydrocarbyl carbonate prepared is dimethyl carbonate. A most preferred manner of preparing dimethyl carbonate involves a continuous, vapor-phase process in which a feed gas comprising about 65 mole percent carbon monoxide, 25 mole percent methanol, and 10 mole percent oxygen is passed over a heterogeneous catalyst comprised of between about 1 and 10 weight percent of copper in the form of a pyridine copper methoxy chloride complex supported on activated carbon, at a temperature of between about 90° C. and 125° C. and a pressure of between 15 and 25 atmospheres.

In the preparation of the dihydrocarbyl carbonates, the use of an activated carbon support for the complex described hereinbefore is critical. The use of activated carbon as a support results in a significantly higher rate of reaction than the use of other commonly known supports. Furthermore, the selectivity of the reaction towards the dihydrocarbyl carbonate based on the amount of carbon monoxide fed to the reaction, is surprisingly higher when activated carbon is used as the support in comparison to other commonly used supports.

The process of this invention preferably results in a 60 mole percent yield of a dihydrocarbyl carbonate based on the carbon monoxide feed, and more preferably a 65 mole percent yield. Selectivity means herein the mole percent of carbon monoxide converted to dihydrocarbyl carbonate. The use of activated carbon as a support for the nitrogen-containing coordination compound copper hydrocarbyloxy halide complex allows a rate of at least 3 times or greater than other known supports, preferably a rate of 4 times or greater than other known supports. Preferably, the catalyst complex of this invention results in a reaction rate 10 times greater than the heterogeneous catalyst of U.S. Pat. No. 3,980,690; more preferably 15 times greater.

SPECIFIC EMBODIMENT

The following example is included for illustrative purposes only and does not limit the scope of the claims or the invention. All parts and percentages are by weight unless otherwise specified.

EXAMPLE

The pyridine oomplex of oopper methoxy chloride is prepared by reacting 24.8 g of cuprous chloride with dry air in the presence of 600 ml of methanol and 40 ml of pyridine for 16 hours. The green precipitate is analyzed as $C_5H_5NCu(OCH_3)Cl$ by elemental and infrared analyses.

$C_5H_5NCu(OCH_3)Cl$ (0.8 g) is dissolved in 20 ml of pyridine, and the solution impregnated onto 12 g of dried activated carbon (Darco®, 12–20 mesh). The dried product is analyzed as 1.47 weight percent copper. Catalyst (1.6 g) is loaded into a ½" outside diameter flow reactor operated at 110° C. and at 20 atmospheres of pressure. A flow consisting of 80 cc(STP)/minute of carbon monoxide and 13 cc(STP)/minute of oxygen is passed through the reactor. Liquid methanol is fed to a vaporizer operated at 185° C. with a LC pump which allows small amounts of methanol to be added to the system under pressure. A flow of methanol vapor of 30 cc(STP)/minute is introduced into the carbon monoxide/oxygen feed stream prior to flowing through the reactor. The reaction is run for 100 hours, and the dimethyl carbonate (DMC) produced is monitored on-line by gas chromatography analysis. The rate of the reaction is 0.0016 moles of DMC/g atom copper/sec. The selectivity of the reaction for dimethyl carbonate, percent dimethyl carbonate based on the carbon monoxide fed to the reactor is 65 percent. Carbon dioxide is the major side product observed along with minor amounts of methyl formate and methyl acetate.

What is claimed is:

1. A process for the preparation of a dihydrocarbyl carbonate which comprises contacting oxygen, carbon monoxide and an alcohol, which can be vaporized under the reaction conditions, in the vapor phase in the presence of a catalyst which comprises a nitrogen-containing coordination compound copper hydrocarbyloxy halide complex supported on activated carbon, under conditions such that a dihydrocarbyl carbonate is prepared.

2. The process of claim 1 wherein the alcohol is a $C_{1-6}$ alkanol, a $C_{3-6}$ cycloalkanol or benzyl alcohol, or mixtures thereof, and the hydrocarbyl groups on the dihydrocarbyl carbonate are separately in each occurrence $C_{1-6}$ alkyl, $C_{3-6}$ cycloalkyl or benzyl.

3. The process of claim 2 wherein one alcohol is used and the dihydrocarbyl carbonate prepared is symmetrical.

4. The process of claim 3 wherein the alcohol is a $C_{1-6}$ alkanol and the dihydrocarbyl carbonate is a $C_{1-6}$-dialkyl carbonate.

5. The process of claim 4 wherein the alcohol is methanol and the dihydrocarbyl carbonate is dimethyl carbonate.

6. The process of claim 4 wherein the basic nitrogen-containing coordination compound is ammonia, a primary amine, a secondary amine, a heterocyclic amine, an aromatic amine or an organic nitrile; the halide is bromine or chlorine; and the hydrocarbyloxy moiety is $C_{3-6}$ cycloalkoxy, benzoxy or $C_{1-6}$ alkoxy.

7. The process of claim 6 wherein the basic nitrogen-containing coordination compound is a trialkylamine, pyridine, a alkyl substituted pyridine, dialkyaminopyridine, imidazole, piperidine, ammonia or acetonitrile; the halide is chlorine; and the hydrocarbyloxy moiety is $C_{1-6}$ alkoxy.

8. The process of claim 7 wherein the basic nitrogen-containing coordination compound is pyridine, a alkyl substituted pyridine dialkyaminopyridine, ammonia or acetonitrile; and the hydrocarbyloxy moiety is propoxy, ethoxy or methoxy.

9. The process of claim 8 wherein the basic nitrogen-containing compound is pyridine or alkyl substituted pyridine dialkyaminopyridine, and the hydrocarbyloxy moiety is methoxy.

10. The process of claim 8 wherein the activated carbon is an acid washed lignite carbon.

11. The process of claim 10 wherein the catalyst contains between about 1 and 10 percent by weight of the activated carbon, of copper.

12. The process of claim 11 wherein the temperature is between about 20° C. and 150° C.

13. The process of claim 12 wherein the pressure is between about 1 and 10 atmospheres.

* * * * *